United States Patent
Klele

(10) Patent No.: US 12,023,363 B2
(45) Date of Patent: *Jul. 2, 2024

(54) NATURAL PRODUCT COMPOSITIONS FOR TREATING OR MANAGING SYMPTOMS OF ADD, ADHD, ANXIETY, AND DEPRESSION

(71) Applicant: Luke Klele, Emerson, NJ (US)

(72) Inventor: Luke Klele, Emerson, NJ (US)

(*) Notice: Subject to any disclaimer, the term of this patent is extended or adjusted under 35 U.S.C. 154(b) by 216 days.

This patent is subject to a terminal disclaimer.

(21) Appl. No.: 17/191,507

(22) Filed: Mar. 3, 2021

(65) Prior Publication Data

US 2021/0275617 A1 Sep. 9, 2021

Related U.S. Application Data

(63) Continuation of application No. 16/806,704, filed on Mar. 2, 2020, now Pat. No. 10,953,056, which is a continuation of application No. 15/985,610, filed on May 21, 2018, now Pat. No. 10,624,939.

(60) Provisional application No. 62/589,916, filed on Nov. 22, 2017, provisional application No. 62/510,156, filed on May 23, 2017.

(51) Int. Cl.
| *A61K 36/00* | (2006.01) |
| *A61K 31/05* | (2006.01) |
| *A61K 31/105* | (2006.01) |
| *A61K 31/352* | (2006.01) |
| *A61K 36/185* | (2006.01) |
| *A61K 36/53* | (2006.01) |
| *A61K 36/81* | (2006.01) |
| *A61K 36/84* | (2006.01) |

(52) U.S. Cl.
CPC ............ *A61K 36/185* (2013.01); *A61K 31/05* (2013.01); *A61K 31/105* (2013.01); *A61K 31/352* (2013.01); *A61K 36/53* (2013.01); *A61K 36/81* (2013.01); *A61K 36/84* (2013.01)

(58) Field of Classification Search
CPC ..................................................... A61K 36/00
See application file for complete search history.

(56) References Cited

FOREIGN PATENT DOCUMENTS

WO WO-2017007833 A1 * 1/2017 ............... A23L 2/52

OTHER PUBLICATIONS

Hayakawa et al., Delayed treatment with cannabidiol has a cerebroprotective action via a cannabinoid receptor-independent myeloperoxidase-inhibiting mechanism, J Neurochem 102(5):1488-1496, 2007.*

* cited by examiner

*Primary Examiner* — Rosanne Kosson
(74) *Attorney, Agent, or Firm* — Charney IP Law LLC; Thomas M. Finetti

(57) ABSTRACT

Disclosed herein are natural product compositions for treating ADHD and related disorders.

13 Claims, No Drawings

NATURAL PRODUCT COMPOSITIONS FOR TREATING OR MANAGING SYMPTOMS OF ADD, ADHD, ANXIETY, AND DEPRESSION

CROSS REFERENCE TO RELATED APPLICATIONS

The present disclosure is a continuation-in-part of U.S. application Ser. No. 16/806,704 filed on Feb. 12, 2020, which is a continuation of U.S. application Ser. No. 15/985,610 filed on May 21, 2018, which application claims priority to and the benefit of the filing date of U.S. Provisional Application No. 62/589,916, filed Nov. 22, 2017 and which also claims priority to and the benefit of the filing date of U.S. Provisional Application No. 62/510,156, filed May 23, 2017, the disclosures of each are hereby incorporated by reference herein in their entireties.

BACKGROUND OF THE DISCLOSURE

Attention deficit disorder/attention deficit hyperactivity disorder (ADD/ADHD) and related disorders are common in children, adolescents and adults. The recent increase in the number of cases of attention deficit hyperactivity disorder (ADHD) and related disorders has been accompanied by a surge in the use of prescription psychopharmacological treatments. Stimulants such as methylphenidate (Ritalin) and amphetamines are the most common type of medication used for treating ADHD. These medications can activate brain circuits that support attention and focused behavior. Ritalin is a class 2 narcotic, with risk of abuse. Other non-stimulant medications, such as atomoxetine, guanfacine, and clonidine, are also available. For many children, ADHD medications reduce hyperactivity and impulsivity and improve their ability to focus, work, and learn. Children taking medications, however, must be monitored closely and carefully for compliancy, and for the commonly reported side-effects such as decreased appetite, sleep problems, anxiety and irritability. Some children report mild stomach aches or headaches. Other, less frequent side effects include cardiovascular or psychiatric problems.

Adults with ADHD are treated with medication, psychotherapy, or a combination of treatments. Adult prescriptions for stimulants and other medications, however, require special considerations, including the need to avoid dangerous drug interactions with commonly used medications for physical problems such as diabetes, high blood pressure, high cholesterol, anxiety and depression etc.

There remains a need for a safe and effective treatment for adult and pediatric ADHD and related disorders.

BRIEF SUMMARY OF THE DISCLOSURE

In one aspect of the present disclosure is a formulation which includes natural ingredients, and which are useful in treating a subject having ADD/ADHD or a related disorder, or one or more symptoms of ADD/ADHD. In another aspect of the present disclosure is a formulation which includes natural ingredients, and which are useful in reducing symptoms ADD/ADHD or a related disorder, or one or more symptoms of ADD/ADHD. In another aspect of the present disclosure is a formulation which includes natural ingredients, and which are useful in managing or controlling symptoms of ADD/ADHD or a related disorder, or one or more symptoms of ADD/ADHD.

In another aspect of the present disclosure is a formulation which includes natural ingredients, and which are useful in treating a subject having anxiety. In another aspect of the present disclosure is a formulation which includes natural ingredients, and which are useful in reducing symptoms of anxiety. In another aspect of the present disclosure is a formulation which includes natural ingredients, and which are useful in managing or controlling symptoms of anxiety.

In another aspect of the present disclosure is a formulation which includes natural ingredients, and which are useful in treating a subject having depression. In another aspect of the present disclosure is a formulation which includes natural ingredients, and which are useful in reducing symptoms of depression. In another aspect of the present disclosure is a formulation which includes natural ingredients, and which are useful in managing or controlling symptoms of depression.

In one aspect of the present disclosure is a natural product composition comprising (i) at least three natural products selected from the group consisting of cannabidiol, spikenard, a root extract from a *valerian* species, passion flower extract, and ashwagandha, and (ii) a pharmaceutically acceptable carrier or excipient. In some embodiments, the natural product composition is free from caffeine or other like stimulants. In some embodiments, the natural product composition is free from theanine.

In some embodiments, the natural product composition comprises at least cannabidiol, spikenard, and a root extract from a *valerian* species. In some embodiments, the natural product composition comprises at least four of a cannabidiol, spikenard, *valerian* root, passion flow extract, and ashwagandha. In some embodiments, the natural product composition comprises at least a cannabidiol, spikenard, a root extract from a *valerian* species, and ashwagandha.

In another aspect of the present disclosure is a multi-component composition including cannabidiol, spikenard, *valerian* root, passion flow extract, and ashwagandha. In some embodiments, the multi-component composition is mixed with a pharmaceutically acceptable carrier or excipient to provide a pharmaceutical formulation. In some embodiments, the pharmaceutical formulation comprises from between about 1% to about 99% by total weight of a carrier or excipient, e.g. water.

In another aspect of the present disclosure is a natural product composition comprising (i) passion flower in an amount ranging from between about 5% to about 17.5% by total weight of the natural product composition; (ii) a root extract from a *valerian* species in an amount ranging from between about 30% to about 60% by total weight of the natural product composition; (iii) Ashwagandha in an amount ranging from between about 10% to about 30% by total weight of the natural product composition; (iv) spikenard in an amount ranging from between about 5% to about 20% by total weight of the natural product composition; and (v) cannabidiol in an amount ranging from between about 2% to about 20% by total weight of the natural product composition. In some embodiments, the natural product composition may be admixed with a pharmaceutically acceptable excipient or carrier to provide a suitable formulation for administration to a patient in need thereof. In some embodiments, a ratio of an amount of a natural product composition to an amount of a pharmaceutically acceptable excipient or carrier ranges from about 10:1 to about 1:10. In some embodiments, the ratio ranges from about 5:1 to about 1:5.

In another aspect of the present disclosure is a method of treating ADHD comprising administering to a subject in need thereof a formulation comprising a comprising (i) a cannabidiol, spikenard, *valerian* root, passion flow extract, and ashwagandha; and (ii) a pharmaceutically acceptable carrier or excipient. In some embodiments, the administration of the formulation does not cause a substantial increase in serotonin levels.

In another aspect of the present disclosure is a method of reducing or ameliorating the symptoms of ADD, ADHD, or related disorders comprising administering to a subject in need thereof a natural product composition comprising (i) a cannabidiol, spikenard, *valerian* root, passion flow extract, and ashwagandha; and (ii) a pharmaceutically acceptable carrier or excipient. In some embodiments, the administration of the natural product composition does not cause a substantial increase in serotonin levels.

In another aspect of the present disclosure is a method of treating anxiety comprising administering to a subject in need thereof a formulation comprising a comprising (i) a cannabidiol, spikenard, *valerian* root, passion flow extract, and ashwagandha; and (ii) a pharmaceutically acceptable carrier or excipient.

In another aspect of the present disclosure is a method of reducing or ameliorating symptoms of anxiety comprising administering to a subject in need thereof a natural product composition comprising (i) a cannabidiol, spikenard, *valerian* root, passion flow extract, and ashwagandha; and (ii) a pharmaceutically acceptable carrier or excipient. In some embodiments, the administration of the natural product composition does not cause a substantial increase in serotonin levels.

In another aspect of the present disclosure is a method of treating depression comprising administering to a subject in need thereof a formulation comprising a comprising (i) a cannabidiol, spikenard, *valerian* root, passion flow extract, and ashwagandha; and (ii) a pharmaceutically acceptable carrier or excipient.

In another aspect of the present disclosure is a method of reducing or ameliorating symptoms of depression comprising administering to a subject in need thereof a natural product composition comprising (i) a cannabidiol, spikenard, *valerian* root, passion flow extract, and ashwagandha; and (ii) a pharmaceutically acceptable carrier or excipient. In some embodiments, the administration of the natural product composition does not cause a substantial increase in serotonin levels.

In another aspect of the present disclosure is a functional food composition or food product comprising a cannabidiol, spikenard, *valerian* root, passion flow extract, and ashwagandha. In some embodiments, the food product is a gelatin (e.g. Jell-O®). In another aspect of the present disclosure is a dietary supplement comprising cannabidiol, spikenard, *valerian* root, passion flow extract, and ashwagandha.

In another aspect of the present disclosure are kits comprising a natural product composition including (i) a cannabidiol, spikenard, *valerian* root, passion flow extract, and ashwagandha; and (ii) a pharmaceutically acceptable carrier or excipient. In some embodiments, the carrier is a food additive. In some embodiments, the kit comprises instructions for combining the natural product composition with the food additive to provide a food product comprising an effective amount of the natural product composition active components. In some embodiments, the kit may include at least one container and at least one label. In some embodiments, suitable containers include, for example, bubble packs, boxes, bottles, vials and tubes. In some embodiments, the containers can be formed from a variety of materials such as glass, metal or plastic.

In another aspect of the present disclosure is a composition comprising (i) an activate pharmaceutical ingredient (API) for treating ADD, ADHD, or a symptom of ADD or ADHD; and (ii) a natural product composition comprising (a) a cannabidiol, spikenard, *valerian* root, passion flow extract, and ashwagandha; and (b) a pharmaceutically acceptable carrier or excipient. In some embodiments, the API and the natural product formulation are administered contemporaneously. In some embodiments, the API and the natural product composition are administered sequentially. In some embodiments, co-administration of the API and the natural product composition synergistically reduces at least one symptom of ADD or ADHD, or a symptom of a related disorder.

In another aspect of the present disclosure is a natural product composition comprising (i) a cannabidiol, (ii) a hemp oil, and (iii) at least one additive selected from the group consisting of passion flower, a root extract from a *valerian* species, Ashwagandha, and spikenard. In some embodiments, the natural product composition further comprises at least two of passion flower, a root extract from a *valerian* species, Ashwagandha, and spikenard. In some embodiments, the natural product composition further comprises at least three of passion flower, a root extract from a *valerian* species, Ashwagandha, and spikenard. In some embodiments, an amount of the cannabidiol ranges from between about 2% to about 20% by total weight of the natural product composition. In some embodiments, an amount of additive ranges from between about 10% to about 90% by total weight of the natural product composition.

In another aspect of the present disclosure is a natural product composition comprising a cannabidiol and at least two additives selected from the group consisting of passion flower, a root extract from a *valerian* species, Ashwagandha, and spikenard. In some embodiments, the composition comprises at least three of the additives. In some embodiments, an amount of the cannabidiol ranges from between about 2% to about 20% by total weight of the natural product composition.

In another aspect of the present disclosure is a method of treating ADHD, or the symptoms thereof, comprising administering to a subject in need thereof a formulation comprising a natural product composition comprising a cannabidiol and at least two additives selected from the group consisting of passion flower, a root extract from a *valerian* species, Ashwagandha, and spikenard, the formulation further comprising at least one pharmaceutically acceptable carrier. In some embodiments, the formulation is administered such that at least 4 mg/kg of the cannabidiol is administered to the subject per day. In some embodiments, the formulation is administered such that at least 6 mg/kg of the cannabidiol is administered to the subject per day. In some embodiments, the formulation is administered such that at least 8 mg/kg of the cannabidiol is administered to the subject per day.

In another aspect of the present disclosure is a method of treating anxiety, or the symptoms thereof, comprising administering to a subject in need thereof a formulation comprising a natural product composition comprising a cannabidiol and at least two additives selected from the group consisting of passion flower, a root extract from a *valerian* species, Ashwagandha, and spikenard; formulation further comprising at least one pharmaceutically acceptable carrier, and wherein the formulation is administered such that at least 4 mg/kg of the cannabidiol is administered to the subject per day.

DETAILED DESCRIPTION

Definitions

It should also be understood that, unless clearly indicated to the contrary, in any methods claimed herein that include more than one step or act, the order of the steps or acts of the method is not necessarily limited to the order in which the steps or acts of the method are recited.

As used herein, the singular terms "a," "an," and "the" include plural referents unless context clearly indicates otherwise. Similarly, the word "or" is intended to include "and" unless the context clearly indicates otherwise. The term "includes" is defined inclusively, such that "includes A or B" means including A, B, or A and B.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of." "Consisting essentially of," when used in the claims, shall have its ordinary meaning as used in the field of patent law.

The terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, the terms "ADD" and "ADHD" are meant to encompass disorders affecting cognitive, learning, and/or memory functions and the associated symptoms. Included are mild cognitive impairment, attention deficit hyperactivity disorder, anxiety disorder, forgetfulness, impulsivity, mental fatigue, difficulty in concentration and focus. Attention Deficit Hyperactivity Disorder (ADHD) is a disorder which may be divided into four subtypes, according to the main features associated with the disorder: inattentiveness, impulsivity, and hyperactivity. The four subtypes are ADHD predominantly impulsivity type, ADHD predominantly inattentive type, ADHD predominantly hyperactive-impulsive type and ADHD not otherwise specified (e.g. Attention Deficit Disorder (ADD)).

As used herein, the term "administering" means providing a composition, formulation, or specific agent to a subject in need of treatment, including those described herein.

As used herein, the term "extract" refers to an alcoholic extract, an alcohol/water extract or an oil-based extract of a material, in particular, a plant component.

The phrases "pharmaceutically acceptable" or "pharmacologically acceptable" refer to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the expression vectors of the present disclosure, its use in therapeutic compositions is contemplated.

As used herein, the term "subject" refers to a mammal such as a human, mouse or primate. Typically, the mammal is a human (*Homo sapiens*). A human subject may be an adult patient or a pediatric patient.

As used herein, the terms "therapeutically effective dose" or "dose amount" refer to an amount of a composition, or a component of the composition, which is effective to achieve an improvement in a subject or his physiological systems including, but not limited to, improved improvement or elimination of symptoms, delayed onset of a disorder, slower progress of symptoms and other indicators selected as appropriate by those skilled in the art.

As used herein, the terms "treatment," "treating," or "treat," with respect to a specific condition, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease and/or relieving one or more disease symptoms. "Treatment" can also encompass delivery of an agent or administration of a therapy in order to provide for a pharmacologic effect, even in the absence of a disease or condition. The term "treatment" is used in some embodiments to refer to administration of a compound of the present disclosure to mitigate a disease or a disorder in a host, preferably in a mammalian subject, more preferably in humans. Thus, the term "treatment" can include includes: preventing a disorder from occurring in a host, particularly when the host is predisposed to acquiring the disease but has not yet been diagnosed with the disease; inhibiting the disorder; and/or alleviating or reversing the disorder. Insofar as the methods of the present disclosure are directed to preventing disorders, it is understood that the term "prevent" does not require that the disease state be completely thwarted. Rather, as used herein, the term preventing refers to the ability of the skilled artisan to identify a population that is susceptible to disorders, such that administration of the compounds of the present disclosure can occur prior to onset of a disease. The term does not mean that the disease state must be completely avoided.

Natural Product Compositions

In general, the present disclosure provides for natural product compositions comprising at least three active components, the active components selected from the group consisting of cannabidiol, spikenard, a root extract from a *valerian* species, passion flower extract, and ashwagandh. In some embodiments, the natural product composition comprises four of the active components. In other embodiments, the natural product composition comprises all of the recited active compounds. Each of the active components of the natural product composition are described herein.

Passion flower, of the family Passifloraceae, is a perennial medicinal plant used in herbal teas for its calming and sedative effect. It includes several hundred species, some of which, such as *Passiflora edulis* and *Passiflora ligularis*, are known to give edible fruits (passion fruit and Sweet Granadilla). Passion flower is a dry powdered herb deriving from *Passiflora incarnata*. Passion flower has been traditionally used for it mild sedative effects; further, it advantageously has a pleasant taste and is surprisingly gentle. It is believed that the plant contains a group of indole alkaloids and several flavonoids which are believed responsible for its sedative and analgesic effects.

In some embodiments, an amount of passion flower within any natural product composition ranges from between about 5% to about 17.5% by total weight of the natural product composition. In other embodiments, an amount of passion flower within any natural product composition ranges from between about 7.5% to about 15% by total weight of the natural product composition. In yet other embodiments, an amount of passion flower within any natural product composition ranges from between about 9% to about 13% by total weight of the natural product composition.

*Valerian* (*Valeriana officinalis* or *valerian edulis*) is a perennial plant native to North America, Asia and Europe. The root has been traditionally used as treatment for anxiety and insomnia. A meta-analysis of available studies suggest that *valerian* root extract may improve sleep absent of side-effects (Bent S, Padula A, Moore D, Patterson M, Mehling W. *valerian* for sleep: a systematic review and meta-analysis. Am J. Med. 2006 December; 119(12):1005-12 Abstract) acting particularly to decrease the time to sleep onset and improved sleep quality in individuals. *valerian* has been shown to modulate Gamma Aminobutyric Acid (GABA) receptors (Yuan C S, Mehendale S, Xiao Y, Aung H H, Xie J T, Ang-Lee M K. The gamma-aminobutyric acidergic effects of *valerian* and valerenic acid on rat brainstem neuronal activity. Anesth Analg. 2004 February; 98(2):353-8). Valerinic acid specifically has been shown to decrease neural activity in the brainstem produced by the GABA receptor antagonist, muscimol. Data from this study suggests that the pharmacological effects of *valerian* extract and valerenic acid are mediated through modulation of GABA(A) receptor function (Yuan C S, Mehendale S, Xiao Y, Aung H H, Xie J T, Ang-Lee M K. The gamma-aminobutyric acidergic effects of *valerian* and valerenic acid on rat brainstem neuronal activity. Anesth Analg. 2004 February; 98(2):353-8). Without wishing to be bound to theory, *valerian* root extract product causes the release of gamma-aminobutyric acid (GABA) and inhibits the action of GABA transaminase, the enzyme that destroys the neurotransmitter.

In some embodiments, the formulation comprises a root extract from a *valerian* species, e.g. *valerian officinalis* or *valerian edulis*. In some embodiments, an amount of a root extract from a *valerian* species within any natural product composition ranges from between about 30% to about 60% by total weight of the natural product composition. In other embodiments, an amount of a root extract from a *valerian* species within any natural product composition ranges from between about 35% to about 55% by total weight of the natural product composition. In yet other embodiments, an amount of a root extract from a *valerian* species within any natural product composition ranges from between about 40% to about 50% by total weight of the natural product composition.

Ashwagandha (Withania somnifera) is an erect shrub found growing wild throughout the hotter parts of India and is cultivated for its roots, which are well known in Ayurveda for their rejuvenative or rasayana properties. Without wishing to be bound by any particular theory, it is believed that the roots contain between about 0.2 and about 0.3% of alkaloids and withaferin A together with several withanolides, which are C-28 steroidal lactones of the ergostane type. In addition, the roots are believed to contain starch, reducing sugars, hentriacontane (C31-normal alkane), and a number of amino acids. Also present are sitoindosides VII and VIII, which are acylsteryl glucosides, and sitoindosides IX and X, which are C-28 glycowithanolides that may contribute to the adaptogenic properties found in this herb. There are several chemotypes of the plant Ashwagandha (Withania somnifera) available with varying amounts of the various sitoindosides. See, M. S. Premila (2007), Ayurvedic Herbs.

Ashwagandha (Withania somnifera) root powder, root methanol extract, and its active principles (a mixture containing equimolar concentrations of withaferin A and sitoindosides VII-X), have been shown to possess antioxidant activity, which may explain the antistress, anti-inflammatory, immunomodulatory, and cognition-enhancing and rejuvenative effects shown in experimental and clinical studies. Withaferin A has been shown to have anti-inflammatory and antiarthritic properties in several experimental models. See, M. S. Premila (2007), Ayurvedic Herbs. Ashwagandha herb can be provided, for example, in Ashwagandha root extract powder, standardized to greater than 5% withanolides by weight.

In some embodiments, an amount of Ashwagandha within any natural product composition ranges from between about 10% to about 30% by total weight of the natural product composition. In other embodiments, an amount of Ashwagandha within any natural product composition ranges from between about 15% to about 27.5% by total weight of the natural product composition. In yet other embodiments, an amount of Ashwagandha within any natural product composition ranges from between about 20% to about 25% by total weight of the natural product composition.

Spikenard (*Nardostachys jatamanse*) is a class of aromatic amber-colored essential oil. Without wishing to be bound by any particular theory, spikenard is considered a calming herb in ayurveda and unani because of its medicinal values. In ayurveda, it is often used against stress, spasm, epilepsy, convulsion and hysteria.

In some embodiments, an amount of spikenard within any natural product composition ranges from between about 5% to about 20% by total weight of the natural product composition. In other embodiments, an amount of spikenard within any natural product composition ranges from between about 7.5% to about 17.5% by total weight of the natural product composition. In yet other embodiments, an amount of spikenard within any natural product composition ranges from between about 10% to about 15% by total weight of the natural product composition.

Without wishing to be bound by any particular theory, it is believed that cannabidiol ("CBD") is non-psychoactive and may act as an anti-inflammatory agent. CBD is a compound belonging to a broader class of cannabinoids. Cannabinoids are a heteromorphic group of chemicals which activate the body's cannabinoid receptors. Initially cannabinoids were discovered in *Cannabis sativa*, the *cannabis* plant. There are three main types of cannabinoids: herbal cannabinoids that occur uniquely in the *cannabis* plant, synthetic cannabinoids that are manufactured and endogenous cannabinoids that are produced in vivo. Herbal cannabinoids are nearly insoluble in water but soluble in lipids, alcohol and non-polar organic solvents. These natural cannabinoids are concentrated in a viscous resin that is produced in glandular structures known as trichomes. In addition to cannabinoids, the resin is rich in terpenes, which are largely responsible for the odor of the *cannabis* plant.

Unlike cannabinoids (e.g. THC), cannabidiols do not bind either the brain receptor CB1 or the peripheral receptors CB2 and therefore does not cause the central or peripheral effects mediated by these receptors. Furthermore, CBD has no psychotropic (cannabimimetic) activity and its molecular structure and properties are substantially different from those of cannabinoids [Science 169: 611-612 (1970); "Marijuana/cannabinoids: neurobiology and neurophysiology," ed. L. Murphy and A. Bartke, CRC Press, Boca Raton, 1-33 (1992)].

In addition to its immunomodulating and anti-inflammatory properties, CBD has been reported to exhibit anticonvulsive, anti-anxiety, and antipsychotic activity, and function as an efficient neuroprotective antioxidant. The in vitro suppressive effect of CBD on down-modulating the release of tumor necrosis factor α (TNFα), interleukin 1 (IL-1), and interferon γ (IFN)-γ from peripheral blood cells has also been reported. CBD has demonstrated activity in ameliorating collagen-induced arthritis in mice and has been shown to suppress T-cell responses and the production of TNFα and IFNγ. CBD also inhibits uptake of THC and anandamide and its hydrolysis. For example, U.S. Pat. No. 6,410,588 describes the use of cannabidiol for treating inflammatory diseases such as rheumatoid arthritis, multiple sclerosis and Crohn's Disease, and medicinal preparations containing CBD for use in treating such diseases. By means of another example, PCT/IL01/00537 describes pharmaceutical compositions comprising cannabidiol derivatives which have analgesic, antianxiety, anticonvulsive, neuroprotective, antipsychotic and anticancer activity.

In some embodiments, cannabidiol refers to 2-[3-methyl-6-(1-methylethenyl)-2-cyclohexen-1-yl]-5-pentyl-1,3-benzenediol as well as to pharmaceutically acceptable salts, solvates, metabolites (e.g., cutaneous metabolites), and metabolic precursors of 2-[3-methyl-6-(1-methylethenyl)-2-cyclohexen-1-yl]-5-pentyl-1,3-benzenediol. The synthesis of 2-[3-methyl-6-(1-methylethenyl)-2-cyclohexen-1-yl]-5-pentyl-1,3-benzenediol is described, for example, in Petilka et al., Helv. Chim. Acta, 52:1102 (1969) and in Mechoulam et al., J. Am. Chem. Soc., 87:3273 (1965), which are hereby incorporated by reference.

In some embodiments, an amount of cannabidiol within any natural product composition ranges from between about 2% to about 20% by total weight of the natural product composition. In other embodiments, an amount of cannabidiol within any natural product composition ranges from between about 4% to about 15% by total weight of the natural product composition. In yet other embodiments, an amount of cannabidiol within any natural product composition ranges from between about 6% to about 11% by total weight of the natural product composition.

In some embodiments, a natural product composition comprises (i) passion flower in an amount ranging from between about 5% to about 17.5% by total weight of the natural product composition; (ii) a root extract from a *valerian* species in an amount ranging from between about 30% to about 60% by total weight of the natural product composition; (iii) Ashwagandha in an amount ranging from between about 10% to about 30% by total weight of the natural product composition; (iv) spikenard in an amount ranging from between about 5% to about 20% by total weight of the natural product composition; and (v) cannabidiol in an amount ranging from between about 2% to about 20% by total weight of the natural product composition.

Pharmaceutically Acceptable Excipients, Carriers, and Additives

The compositions of the present disclosure may further comprise one or more pharmaceutically acceptable excipients including, but not limited to, diluents, binders, lubricants, disintegrants, flavoring agents, taste-masking agents, coloring agents, pH modifiers, stabilizers, absorption enhancers, viscosity modifiers, film forming polymers, bulking agents, surfactants, glidants, plasticizers, preservatives, essential oils and sweeteners. In some embodiments, the pharmaceutically acceptable excipients, carriers, and/or additives may be a food composition or a food product into which the natural product compositions described herein may be introduced.

A person skilled in the art will be able to select the suitable excipients or mixtures of excipients for the desired natural product composition. In general, the amount of any pharmaceutically acceptable excipient, carrier, and/or additive included within any natural product composition may vary depending on the desired effect, route of administration, form of the final composition. In general, however, a total amount of pharmaceutically acceptable excipients, carriers, and/or additives formulated with the natural product compositions may range from about 1% to about 99% by total weight of the composition. In other embodiments, the total amount of pharmaceutically acceptable excipients, carriers, and/or additives formulated with the natural product compositions may range from about 1% to about 9% by total weight of the composition. In other embodiments, the total amount of pharmaceutically acceptable excipients, carriers, and/or additives formulated with the natural product compositions may range from about 1% to about 80% by total weight of the composition. In yet other embodiments, the total amount of pharmaceutically acceptable excipients, carriers, and/or additives within the natural product compositions may range from about 1% to about 50% by total weight of the composition. In other embodiments, the total amount of pharmaceutically acceptable excipients, carriers, and/or additives formulated with the natural product compositions may range from about 5% to about 50% by total weight of the composition. By way of example only, a formulation may comprise a 50:50 mixture of any of a natural product composition and a pharmaceutically acceptable excipient, carrier, and/or additive.

In some embodiments, a ratio of an amount of a natural product composition and an amount of a pharmaceutically acceptable excipient or carrier ranges from about 100:1 to about 1:100. In some embodiments, a ratio of an amount of a natural product composition and an amount of a pharmaceutically acceptable excipient or carrier ranges from about 50:1 to about 1:50. In some embodiments, a ratio of an amount of a natural product composition and an amount of a pharmaceutically acceptable excipient or carrier ranges from about 25:1 to about 1:25. In some embodiments, a ratio of an amount of a natural product composition and an amount of a pharmaceutically acceptable excipient or carrier ranges from about 10:1 to about 1:10. In some embodiments, a ratio of an amount of a natural product composition and an amount of a pharmaceutically acceptable excipient or carrier ranges from about 5:1 to about 1:5.

In some embodiments, the carrier is water. In some embodiments, an amount of water present in the composition ranges from about 90% to about 98% by total weight of the composition, from about 90% to about 97% by total weight of the composition, from about 90% to about 96% by total weight of the composition, from about 90% to about 95% by total weight of the composition, from about 90% to about 94% by total weight of the composition, from about 90% to about 93% by total weight of the composition, from about 90% to about 92% by total weight of the composition, and from about 90% to about 91% by total weight of the composition.

A diluent may be selected from, for example, calcium carbonate, calcium phosphate dibasic, calcium phosphate tribasic, calcium sulfate, microcrystalline cellulose, microcrystalline silicified cellulose, powdered cellulose, dextrate, dextrose, fructose, lactitol, lactose anhydrous, lactose monohydrate, lactose dihydrate, lactose trihydrate, mannitol, sorbitol, starch, pregelatinized starch, sucrose, talc, xylitol, maltose, maltodextrin, maltitol.

A binder may be selected from, for example, acacia, alginic acid, carbomer, carboxymethylcellulose calcium, carbomethylcellulose sodium, microcrystalline cellulose, powdered cellulose, ethyl cellulose, gelatin liquid glucose, guar gum, hydroxyethyl cellulose, hydroxypropyl cellulose, hydroxypropylmethyl cellulose, maltodextrin, methylcellulose, polydextrose, polyethtylene oxide, povidone, sodium alginate, starch paste, pregelatinized starch, sucrose, tragacanth, low-substituted hydroxypropyl cellulose, glucose, sorbitol.

A suitable filler may be selected from, for example, starch derivatives, such as corn starch, potato starch or rice starch, polysaccharides such as dextrins, maltodextrins, dextrates, microcrystalline cellulose, powdered cellulose, mixture of microcrystalline cellulose and guar gum, coprocessed blends of microcrystalline cellulose; and polyhydric alcohols, such as xylitol and sorbitol.

A disintegrant may be selected from, for example, alginic acid, carbon dioxide, carboxymethylcellulose calcium, carboxymethylcellulose sodium, microcrystalline cellulose, powdered cellulose, croscarmelose sodium, crospovidone, sodium docusate, gaur gum, hydroxypropyl cellulose, methylcellulose, polacrilin potassium, poloxamer, povidone, sodium alginate, sodium glycine carbonate, sodium lauryl sulfate, sodium starch glycolate, starch, pregelatinized starch, low-substituted hydroxypropyl cellulose.

A glidant may be selected from, for example, calcium silicate, powdered cellulose, starch, talc, colloidal silicon dioxide.

A lubricant may be selected from, for example, magnesium stearate, stearic acid, sodium stearyl fumarate, magnesium lauryl sulphate, talc, polyethylene glycol, and glyceryl behenate.

A suitable essential oil may be selected from Bergamot oil (extracted from Citrus aurantium L. subsp. bergamia Wright et Arn.); Ylang ylang oil (extracted from *Cananga odorata* Hook. f. and Thoms.); Jasmine essential oil (extracted from *Jasminum officinale* L.). In one embodiment, a mixture of essential oils comprises equal portions totaling about 0.01% to about 1% w/w, preferably about 0.1% w/w of the total composition. Other essential oils are possible.

A suitable sweetener may be selected from sugars such as sucrose, lactose and glucose; cyclamate and salts thereof; saccharin and salts thereof; and aspartame.

Flavoring agents may be incorporated in the composition may be chosen from synthetic flavors oils and flavoring aromatics, natural oils, plant extracts. Examples include cinnamon oil, oil of wintergreen, peppermint oil, clove oil, bay oil, anise oil, *eucalyptus*, thyme oil, cedar leaf oil, nutmeg oil, sage oil or almond oil. Examples of flavoring agents include, but are not limited to, almond, apple, banana, berry, bubblegum, caramel, citrus, cherry, chocolate, coconut, grape, green tea, honey, lemon, licorice, lime, mango, maple, mint, orange, peach, pineapple, raisin, strawberry, vanilla, watermelon and combinations thereof. Flavors may be present in an amount ranging from about 0.05 to about 3 percent by weight based upon the weight of the composition. In some embodiments, the flavoring agent may be selected from natural or synthetic flavors such as, for example, strawberry flavor, wild cherry flavor, green apple flavor, spearmint flavor and peppermint flavor.

Absorption enhancers for use in accordance with certain embodiments of the present disclosure include, for example, Gelucire 44/14; Gelucire 50/13; Tagat TO; Tween 80; isopropyl myristate, polysorbates, sorbitan esters, poloxamer block copolymers, PEG-35 castor oil, PEG-40 hydrogenated castor oil, caprylocaproyl macrogol-8 glycerides, PEG-8 caprylic/capric glycerides, sodium lauryl sulfate, dioctyl sulfosuccinate, polyethylene lauryl ether, ethoxydiglycol, propylene glycol mono-di-caprylate, glycerol monocaprylate, glyceryl fatty acids (C8-C18) ethoxylated, oleic acid, linoleic acid, glyceryl caprylate/caprate, glyceryl monooleate, glyceryl monolaurate, caprylic/capric triglycerides, ethoxylated nonylphenols, PEG-(8-50) stearates, olive oil PEG-6 esters, triolein PEG-6 esters, lecithin, d-alpha tocopheryl polyethylene glycol 1000 succinate, polycarbonate, sodium glycocholate, sodium taurocholate, cyclodextrins, citric acid, sodium citrate, triacetin, combinations thereof, and the like. In certain preferred embodiments, the absorption enhancer is triacetin. In certain embodiments where an absorption enhancer is included in the formulation, the absorption enhancer is included in an amount of from about 0.001% to about 10% by weight of the formulation, preferably in an amount of about 0.01% to about 5% by weight of the formulation.

Routes of Administration and Dosage Forms

Administration to a subject of the natural product compositions according to the present disclosure may be via any common route so long as the target tissue is available via that route. The natural product compositions may conveniently be presented in dosage unit form and may be prepared by any of the methods well known in the art of pharmacy. All methods include the step of bringing the natural product composition (or the individual components thereof) into association with an excipient or carrier. In general, the natural product compositions are prepared by uniformly and intimately bringing the active components into association with a liquid carrier or a finely divided solid carrier or both, and then, if necessary, shaping the product into the desired dosage form. In the natural product compositions, the active components are included in an amount sufficient to produce the desired pharmacologic effect.

Food Products

A food product, dietary composition or supplement according to the present disclosure is any ingestible preparation that contains the natural product compositions of the present disclosure mixed with a food product or dietary supplement composition. The food product can be dried, cooked, boiled, lyophilized or baked. A food composition or food product can comprise a bakery product, including but not limited to bread, pastries, brownies, cakes, pies, donuts, crackers, and muffins. A food composition or food product can comprise a dairy product, including but not limited to milk, fermented milk, curd, whey, yogurt, cream, cheese, butter, clarified butter, ghee, and ice cream. A food composition or food product can comprise a nut butter or seed butter, including but not limited to peanut butter, almond butter, cashew butter, hazelnut butter, macadamia nut butter, pecan butter, pistachio butter, walnut butter, pumpkin seed butter, sesame seed butter, soybean butter, and sunflower seed butter. A food composition or food product can comprise an oil (e.g., a cooking oil), including but not limited to olive oil, coconut oil, vegetable oil, canola oil, corn oil, peanut oil, sunflower seed oil, almond oil, avocado oil, rice bran oil, cottonseed oil, flaxseed oil, linseed oil, grape seed oil, hemp oil, mustard oil, macadamia oil, palm oil, tea seed oil, walnut oil, margarine, lard, butter, clarified butter, ghee, or tallow. A food composition or food product can comprise sports food products such as energy gels, sports drinks, energy powders, energy bars, energy shots, protein powders, and protein drinks (e.g., protein shakes). A food composition or food product can comprise a beverage, including but not limited to water, electrolyte drinks, soda, coconut water, tea (e.g., Jun tea, black tea, green tea, white tea, herbal tea), coffee, a soft drink, an alcoholic beverage (e.g., cocktail, liquor, spirits, beer, wine, malt beverage), water, juice (e.g., apple juice, orange juice, tomato juice, vegetable juice, cranberry juice), a sports drink, electrolyte-enriched water, vitamin-enhanced water, milk (e.g., dairy-based milk, coconut milk, almond milk, soy milk, hemp milk, rice milk, oat milk, cashew milk, hazelnut milk), and yogurt.

A food composition or food product may include the natural product composition disclosed herein within a gelatin-based product (e.g. Jell-O®) or gelatin-based desert. In some embodiments, the food composition or food product comprises the natural product composition and a gelling agent. Suitable examples of gelling agents include carrageenans, agar, sodium alginate, gellan gum, xanthan gum, sodium carboxymethyl cellulose, guar gum, soybean protein, and crystalline cellulose. The amount of the gelling agent contained within the food composition or food product is not limited provided that the effect of the present disclosure is obtained. The proportion of the gelling agent in the food composition is, for example, about 0.5 to about 3 by total weight of the food composition or food product. Without wishing to be bound by any particular theory, it is believed that the amount of the gelling agent contained affects the hardness in mastication. If the amount of gelling agent is less than about 0.5 by total weight of the food composition or food product, the food composition or food product tends to become overly soft, and cannot achieve a hardness suitable for mastication. If, on the other hand, the amount is more than about 3 by total weight of the food composition or food product, the food composition or food products tends to fail to achieve a hardness at which chewing can be performed, even if the number of mastications is increased.

In some embodiments, food products are specifically formulated for pediatric patients, thereby providing a dosage form that is appealing to the patient. For example, a food product may comprise a gelatin-based product whereby a suitable pediatric dose of a natural product composition is contained therein, along with flavoring agents and/or agents that create a desirable mouthfeel. In this way, it is believed that administration to a pediatric patient may be facilitated. It is also believed that such a food product avoids additional stresses associated with taking liquid dosage forms which may have unpleasant tastes, aftertastes, or textures. It is also believed that such a food product avoids the need for swallowing a solid dosage form, which may be difficult for a pediatric patient.

Oral Dosage Forms

The natural product compositions containing the active components may be provided, in general, in the form of discrete units such as hard or soft capsules, tablets, troches or lozenges, each containing a predetermined amount of the active components; in the form of a dispersible powder or granules; in the form of a solution or a suspension in an aqueous liquid or non-aqueous liquid; in the form of syrups or elixirs; or in the form of an oil-in-water emulsion or a water-in-oil emulsion.

Liquid dosage forms for oral administration include, but are not limited to, pharmaceutically acceptable emulsions, solutions, suspensions, syrups and elixirs. In addition to the natural product compositions active components described herein, any liquid dosage forms may contain inert diluents commonly used in the art. For instance, liquid formulations can contain water, alcohol, polyethylene glycol ethers, or any other pharmaceutically acceptable solvents. Solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof may also be present in the inventive compositions. Additionally, oral compositions can include adjuvants such as wetting agents, emulsifying and suspending agents, sweetening, flavoring, and perfuming agents. When formulated as a suspension, the inventive compositions contain the cannabinoid extract and suspending agents, for example, ethoxylated isostearyl alcohols, polyoxyethylene sorbitol, sorbitan esters, microcrystalline cellulose, aluminum metahydroxide, bentonite, agar-agar, tragacanth, and mixtures thereof.

Aqueous suspensions normally contain the natural product composition active components in admixture with excipients suitable for the manufacture of aqueous suspensions. Such excipients may be (a) suspending agents such as hydroxy ethylcellulose, sodium carboxymethylcellulose, methylcellulose, hydroxypropylmethylcellulose, sodium alginate, polyvinylpyrrolidone, gum tragacanth and gum acacia; (b) dispersing or wetting agents which may be (b.1)

a naturally-occurring phosphatide such as lecithin, (b.2) a condensation product of an alkylene oxide with a fatty acid, for example, polyoxyethylene stearate, (b.3) a condensation product of ethylene oxide with a long chain aliphatic alcohol, for example heptadecaethyleneoxycetanol, (b.4) a condensation product of ethylene oxide with a partial ester derived from a fatty acid and a hexitol such as polyoxyethylene sorbitol monooleate, or (b.5) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents, such as sucrose or saccharin.

Oily suspensions may be formulated by suspending the natural product composition active components in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be prepared by the addition of an antioxidant such as ascorbic acid.

Dispersible powders and granules are suitable for the preparation of an aqueous suspension. They provide the natural product composition active components separately in admixture with a dispersing or wetting agent, a suspending agent and one or more preservatives. Suitable dispersing or wetting agents and suspending agents are exemplified by those already described herein. Additional excipients, for example, those sweetening, flavoring and coloring agents described above may also be present, including each of those described herein.

The pharmaceutical compositions of the disclosure may also be in the form of oil-in-water emulsions. The oily phase may be a vegetable oil such as olive oil or *arachis* oils, or a mineral oil such as liquid paraffin or a mixture thereof.

Suitable emulsifying agents may be (a) naturally-occurring gums such as gum acacia and gum tragacanth, (b) naturally-occurring phosphatides such as soybean and lecithin, (c) esters or partial esters derived from fatty acids and hexitol anhydrides, for example, sorbitan monooleate, (d) condensation products of said partial esters with ethylene oxide, for example polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a preservative and flavoring and coloring agents.

Solid dosage forms suitable for oral administration include, capsules, tablets, pills, powders, and granules. The natural product compositions disclosed herein may also be formulated into candies, lollipops, lozenges, etc. In such solid dosage forms, the natural product compositions may be mixed with at least one pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. For capsules, tablets and pills, the dosage form can also comprise buffering agents.

In some embodiments, natural product compositions for oral use may be in the form of hardgelatin or IPMC capsules wherein the active components are mixed with an inert solid diluent, for example pregelatinized starch, calcium carbonate, calcium phosphate or kaolin, or dispensed via a pellet formulation. They may also be in the form of soft gelatin capsules wherein the active ingredient is mixed with water or an oil medium, for example peanut oil, liquid paraffin, medium chain triglycerides or olive oil. A medium chain triglyceride or MCT as that term is used herein, refers to a saturated fat containing from 6-12 carbon atoms. More particularly MCTs comprise substantially 100% C8-C10 fatty acid triglycerides. MCTs are preferably produced by esterifying glycerol with medium chain fatty acids. MCT materials useful in the invention are available, for example, from the Stepan Company of Northfield, Ill. under the trademark NEOBEE®, e.g., NEOBEE® 1095. Other examples of MCT oil to be used in the compositions of the present invention are TCM (trade name) being a mixture of triglycerides wherein about 95% (w/v) of the fatty acid chains have either 8 or 10 carbon atoms Societe des Oleagineaux, France), Miglyol 812 (trade name being a mixed triester of glycerine and caprilic and capric acids—Dynamit Nobel, Sweden).

The tablets, capsules or pellets may be uncoated or they may be coated by known techniques to delay disintegration and absorption in the gastrointestinal tract and thereby provide a delayed action or sustained action over a longer period. For example, a time delay material such as celluloseacetate phtalate or hydroxypropylcellulose acetate succinate or sustained release material such as ethylcellulose or ammoniomethacrylate copolymer (type B) may be employed.

Topical Administration

Dosage forms for topical administration include, but are not limited to, ointments, creams, emulsions, lotions, gels, sunscreens and agents that favor penetration within the epidermis. Various additives, known to those skilled in the art, may be included in the topical formulations of the present disclosure. Examples of additives include, but are not limited to, solubilizers, skin permeation enhancers, preservatives (e.g., anti-oxidants), moisturizers, gelling agents, buffering agents, surfactants, emulsifiers, emollients, thickening agents, stabilizers, humectants, dispersing agents and pharmaceutical carriers. Examples of moisturizers include jojoba oil and evening primrose oil. Suitable skin permeation enhancers are well known in the art and include lower alkanols, such as methanol ethanol and 2-propanol; alkyl methyl sulfoxides such as dimethylsulfoxide (DMSO), decylmethylsulfoxide (C10 MSO) and tetradecylmethyl sulfoxide; pyrrolidones, urea; N,N-diethyl-m-toluamide; $C_2$-$C_6$ alkanediols; dimethyl formamide (DMF), N,N-dimethylacetamide (DMA) and tetrahydrofurfuryl alcohol. Examples of solubilizers include, but are not limited to, hydrophilic ethers such as diethylene glycol monoethyl ether (ethoxydiglycol, available commercially as Transcutol®) and diethylene glycol monoethyl ether oleate (available commercially as Softcutol®); polyoxy 35 castor oil, polyoxy 40 hydrogenated castor oil, polyethylene glycol (PEG), particularly low molecular weight PEGs, such as PEG 300 and PEG 400, and polyethylene glycol derivatives such as PEG-8 caprylic/capric glycerides (available commercially as Labrasol®); alkyl methyl sulfoxides, such as DMSO; pyrrolidones, DMA, and mixtures thereof.

Vape Compositions, Vapor Phase Compositions, or Inhalable Compositions

In some embodiments, the dosage form is a vape composition, such as for pulmonary administration. In some embodiments, the vape composition includes one or more polyols. Examples of suitable polyols include 1,3-butanediol (e.g., racemic), 1,2-butanediol (e.g., racemic), 2,3-butanediol (e.g., racemic), 1,2,5-pentanetriol (e.g., racemic), 1,3,5-pentanetriol (e.g., racemic), 2,4-pentanediol (e.g., racemic), 1,2-pentanediol (e.g., racemic), and 1,2,6-hexanetriol (e.g., racemic). Based in part on their low toxicity (LD50), the polyols serve as desirable, low-boiling-point alternatives to propylene glycol. Further, their characteristics also serve to offset the need for 1,2,3-propanetriol as a co-excipient commonly found in vaping excipients. In an embodiment, the compositions do not solely comprise propane-1,2-diol and/or 1,2,3-propanetriol. In another embodiment, the compositions do not comprise propane-1,2-diol and/or 1,2,3-propanetriol. Polyols are commercially available or can be manufactured using methods known in the art.

In various embodiments, the polyol is a tetraol (e.g., (2R, 3S) butane-1,2, 3,4-tetraol (erythritol) and (2R,3R)-butane-1,2,3,4-tetraol (threitol)), a pentol (e.g., (2R,4R)-pentane-1,2,3,4,5-pentol (arabitol), (2R,4S)-pentane-1,2,3,4,5-pentol (xylitol), (2R,3S,4S)-pentane-1,2,3,4,5-pentol (ribitol), and (2R,3S, 4R,5(S)-hexane-1, 2,3, 4,5-pentol (fucitol)), a hexol (e.g., (2R,3R,4R,5R)-hexan-1,2,3,4,5,6-hexol (mannitol), (2S,3R,4R,5R)-hexane-1,2,3,4,5,6-hexol (sorbitol), (2R,3^,4R,55)-hexane-1,2,3,4,5,6-hexol (galactitol), and (2R,3S, 4S,5R)-hexane-1,2,3,4,5,6-hexol "iditol")), a heptol (e.g., (2R,3R,5R,6R)-heptane-1,2,3,4,5,6,7-heptol (volemitol) and (2S,35',55',65)-heptane-1,2,3,4,5,6,7-heptol (perseitol)).

In some embodiments, the polyol is a polyol ether. Examples of suitable polyol ethers include isomalt ((2R,3R,4R,5R)-6-[[(2S,3R,4S,5S,6R)-3,4,5-trihydroxy-6-(hydroxymethyl)-2-tetrahydropyranyl]oxy]hexane-1, 2,3, 4,5-pentol), lactitol (4-O-a-D-galactopyranosyl-D-glucitol), and maltitol (4-O-a-D-glucopyranosyl-D-glucitol).

The vape compositions may also include one or more solubilizing compounds (also referred to herein as co-solute compounds). The solubilizing compounds may also be active compounds. The solubilizing compounds are polar (e.g., modestly polar compounds), non-polar, or complex non-polar compounds that increase the solubility of the one or more active compounds in the composition. The solubilizing compounds may be planar and have both polar and nonpolar regions that reduce hydrophobic interactions. Without intending to be bound by any particular theory, it is considered that the solubilizing compound forms adducts with the polyol(s) and/or disruptive compound(s). Compositions comprising on or more solubilizing compounds may form hydrotropes. Combinations of solubilizing compounds may be used in the compositions. The solubilizing compounds may be present in the compositions at 1 to 40 mol %, including all integer mol % values and ranges there between.

In some embodiments, the vape composition includes one or more flavorants in an amount ranging from about 0.01% to about 15% by total weight (e.g., about 1% to about 12%, about 2% to about 10%, or about 5% to about 8%) of the vape composition.

In some embodiments, the vape compositions described herein include a natural product composition (such as described herein) and a water-miscible solvent, including, but not limited to, selected from the group consisting of propylene glycol, glycerol, ethanol and a combination thereof. Propylene glycol, having a boiling point of 188.2° C. and glycerol having a boiling point of 290° C., act as solvents and as thickening agents. Propylene glycol, glycerol and ethanol also provide a relatively even heating of the inhalable composition as it is vaporized by the apparatus.

In some embodiments, the vape compositions include about 0 wt. %, 1 wt. %, 2 wt. %, 3 wt. %, 4 wt. %, 5 wt. %, 6 wt. %, 7 wt. %, 8 wt. %, 9 wt. %, 9.5 wt. %, 10 wt. %, 10.5 wt. %, 11 wt. %, 12 wt. %, 13 wt. %, 14 wt. %, 15 wt. %, 16 wt. %, 17 wt. %, 18 wt. %, 19 wt. %, 20 wt. %, 30 wt. %, 40 wt. %, 50 wt. % or a percentage between any two of these values of propylene glycol relative to the of the entire vape composition. In some embodiments, the inhalable composition comprises propylene glycol and does not contain glycerol.

In some embodiments, a quantity of glycerol that is added to the vape compositions comprises 0 wt. %, 1 wt. %, 2 wt. %, 3 wt. %, 4 wt. %, 5 wt. %, 6 wt. %, 7 wt. %, 8 wt. %, 9 wt. %, 9.5 wt. %, 10 wt. %, 10.5 wt. %, 11 wt. %, 12 wt. %, 13 wt. %, 14 wt. %, 15 wt. %, 16 wt. %, 17 wt. %, 18 wt. %, 19 wt. %, 20 wt. %, 30 wt. %, 40 wt. %, 50 wt. % or a percentage between any two of these values of glycerol relative to the of the entire vape composition. In some embodiments, the inhalable composition comprises glycerol and does not contain propylene glycol.

In some embodiments, a quantity of ethanol that is added to the vape compositions comprises 0 wt. %, 1 wt. %, 2 wt. %, 3 wt. %, 4 wt. %, 5 wt. %, 6 wt. %, 7 wt. %, 8 wt. %, 9 wt. %, 9.5 wt. %, 10 wt. %, 10.5 wt. %, 11 wt. %, 12 wt. %, 13 wt. %, 14 wt. %, 15 wt. %, 16 wt. %, 17 wt. %, 18 wt. %, 19 wt. %, 20 wt. %, 30 wt. %, 40 wt. %, 50 wt. % or a percentage between any two of these values of ethanol relative to the of the entire vape composition. In some embodiments, the inhalable composition comprises ethanol and does not contain glycerol or propylene glycol.

In some embodiments, the vape composition described herein comprises propylene glycol and glycerol, each in any of the wt % amounts described herein, such that the vape composition has a wt/wt % ratio of propylene glycol to glycerol (i.e., propylene glycol:glycerol) of 1:1,000, 1:500, 1:100, 1:50, 1:25, 1:20, 1:15, 1:10, 1:5, 1:4, 1:3, 1:2, 1.1.5, 1:1.4, 1:1.3, 1:1.2, 1:1.1, 1:1, 1.1:1, 1.2:1, 1.3:1, 1.4:1, 1.5:1, 2:1, 3:1, 4:1, 5:1, 10:1, 15:1, 20:1, 25:1, 50:1, 100:1, 1,000:1 or a ratio between any two of these values. In some embodiments, the vape composition comprises propylene glycol and glycerol, and the vape composition has a ratio of propylene glycol to glycerol of about 2:1 to about 1:2.

In some embodiments, the vape composition described herein comprises propylene glycol and ethanol, each in any of the wt % amounts described herein, such that the vape composition has a wt/wt % ratio of propylene glycol to ethanol (i.e., propylene glycol:ethanol) of 1:1,000, 1:500, 1:100, 1:50, 1:25, 1:20, 1:15, 1:10, 1:5, 1:4, 1:3, 1:2, 1.1.5, 1:1.4, 1:1.3, 1:1.2, 1:1.1, 1:1, 1.1:1, 1.2:1, 1.3:1, 1.4:1, 1.5:1, 2:1, 3:1, 4:1, 5:1, 10:1, 15:1, 20:1, 25:1, 50:1, 100:1, 1,000:1 or a ration between any two of these values. In some embodiments, the vape composition comprises propylene glycol and ethanol, and the vape composition has a ratio of propylene glycol to ethanol of about 2:1 to about 1:2.

In some embodiments, the vape composition described herein comprises ethanol and glycerol, each in any of the wt % amounts described herein, such that the vape composition has a wt/wt % ratio of ethanol to glycerol (i.e., ethanol:glycerol) of 1:1,000, 1:500, 1:100, 1:50, 1:25, 1:20, 1:15, 1:10, 1:5, 1:4, 1:3, 1:2, 1.1.5, 1:1.4, 1:1.3, 1:1.2, 1:1.1, 1:1, 1.1:1, 1.2:1, 1.3:1, 1.4:1, 1.5:1, 2:1, 3:1, 4:1, 5:1, 10:1, 15:1, 20:1, 25:1, 50:1, 100:1, 1,000:1 or a ration between any two of these values. In some embodiments, the vape composition comprises ethanol and glycerol, and the vape composition has a ratio of ethanol to glycerol of about 2:1 to about 1:2.

Other inhalable compositions or components suitable for formulating the natural product formulations (such as those disclosed herein) into inhalable compositions or vape compositions include those described in United States Patent Application Nos. 2017/0341850, 2017/0079322, 2015/0013695, 2014/0377355, 2014/0377357, and 2015/0297516, the disclosures of which are each hereby incorporated by reference herein in their entireties.

Dosing and Dosing Schedules

One of ordinary skill will appreciate that effective amounts of the components in the formulations used in the methods of the present disclosure can be determined empirically. It will be understood that, when administered to a patient, the total daily usage of the formulation of the present disclosure will be decided by the attending physician or other medical professional within the scope of sound medical judgment. The specific therapeutically effective dose level for any patient will depend upon a variety of factors: the type and degree of the response to be achieved; the activity of the specific composition employed; the age, body weight, general health, sex and diet of the patient; the duration of the treatment; drugs used in combination or coincidental with the method of the present disclosure; and like factors well known in the medical arts.

In some embodiments, an amount of passion flower provided per dose ranges from between about 125 mg to about 500 mg. In other embodiments, an amount of passion flower provided per dose ranges from between about 175 mg to about 400 mg. In yet other embodiments, an amount of passion flower provided per dose ranges from between about 200 mg to about 300 mg. In further embodiments, an amount of passion flower provided per dose is about 250 mg. In some embodiments, passion flower is administered in an amount ranging from about 4 mg/kg/day to about 20 mg/kg/day. In some embodiments, passion flower is administered in an amount ranging from about 6 mg/kg/day to about 12 mg/kg/day.

In some embodiments, an amount of a root extract from a *valerian* species provided per dose ranges from between about 500 mg to about 1500 mg. In other embodiments, an amount of a root extract from a *valerian* species provided per dose ranges from between about 750 mg to about 1250 mg. In yet other embodiments, an amount of a root extract from a *valerian* species provided per dose ranges from between about 900 mg to about 1100 mg. In further embodiments, an amount of a root extract from a *valerian* species provided per dose is about 1000 mg. In some embodiments, a root extract from a *valerian* species is administered in an amount ranging from about 10 mg/kg/day to about 50 mg/kg/day. In some embodiments, a root extract from a *valerian* species is administered in an amount ranging from about 15 mg/kg/day to about 45 mg/kg/day.

In some embodiments, an amount of Ashwagandha provided per dose ranges from between about 250 mg to about 1000 mg. In other embodiments, an amount of Ashwagandha provided per dose ranges from between about 300 mg to about 700 mg. In yet other embodiments, an amount of Ashwagandha provided per dose ranges from between about 400 mg to about 600 mg. In further embodiments, an amount of Ashwagandha provided per dose is about 500 mg. In some embodiments Ashwagandha is administered in an amount ranging from about 7.5 mg/kg/day to about 20 mg/kg/day. In some embodiments, Ashwagandha is administered in an amount ranging from about 10 mg/kg/day to about 30 mg/kg/day.

In some embodiments, an amount of spikenard provided per dose ranges from between about 150 mg to about 600 mg. In other embodiments, an amount of spikenard provided per dose ranges from between about 200 mg to about 500 mg. In yet other embodiments, an amount of spikenard provided per dose ranges from between about 250 mg to about 350 mg. In further embodiments, an amount of spikenard provided per dose is about 350 mg. In some embodiments spikenard is administered in an amount ranging from about 4.5 mg/kg/day to about 24 mg/kg/day. In some embodiments, spikenard is administered in an amount ranging from about 6 mg/kg/day to about 15 mg/kg/day.

In some embodiments, an amount of cannabidiol provided per dose ranges from between about 100 mg to about 400 mg. In other embodiments, an amount of cannabidiol provided per dose ranges from between about 150 mg to about 250 mg. In yet other embodiments, an amount of cannabidiol provided per dose ranges from between about 175 mg to about 225 mg. In further embodiments, an amount of cannabidiol provided per dose is about 200 mg. In some embodiments cannabidiol is administered in an amount ranging from about 3 mg/kg/day to about 16 mg/kg/day. In some embodiments, cannabidiol is administered in an amount ranging from about 4 mg/kg/day to about 12 mg/kg/day.

In some embodiments, the natural product composition is administered once per day. In other embodiments, the natural product composition is administered twice per day. In other embodiments, the natural product composition is administered at least three times per day. In some embodiments, the natural product composition may be administered every 12 hours. In other embodiments, the natural product composition may be administered every 8 hours. In yet other embodiments, the natural product composition may be administered every 4 hours. In even further embodiments, the natural product composition may be administered on an as-needed basis, but where the number of dosages in a 24-hour period does not exceed a predetermined number of doses or a predetermined amount of each active component. In some embodiments, the natural product composition is administered with food. In other embodiments, the natural product composition is administered while in a fasted state.

Any of the natural product compositions described herein can be provided in a unit dosage form. A unit dosage is a total amount of all of the active components within the natural product compositions, which may delivered alone or in combination with other components, and which is to be administered to a subject at or about one time point. Other components which can be included with a unit dosage include, but are not limited, food carriers (e.g. gelatin or gelatin substitutes), dairy products, oils, beverages, such as denoted herein. A unit dosage of a natural product composition may comprise about 1000, 1250, 1500, 1750, 2000, 2500, 3000, 3250, 3500, 3750, 4000, 4250, 4500, 4750, 5000, 5250, 5500, 5750 or more milligrams (mg) of combined active components. A unit dosage of a natural product composition may comprise at least about 1000, 1250, 1500, 1750, 2000, 2500, 3000, 3250, 3500, 3750, 4000, 4250, 4500, 4750, 5000, 5250, 5500, 5750 or more milligrams (mg) of combined active components. A unit dosage of a natural product composition may comprise at most about 1000, 1250, 1500, 1750, 2000, 2500, 3000, 3250, 3500, 3750, 4000, 4250, 4500, 4750, 5000, 5250, 5500, 5750 or more milligrams (mg) of combined active components. A unit dosage can be an hourly dosage. A unit dosage can be a daily dosage. A unit dosage can provide about 1/24, 1/12, 1/8, 1/6, 1/4, 1/3, 1/2, or all of a daily dosage of one or more natural product compositions for a subject in need thereof. As noted herein, a unit dosage can take the form of a tablet, gel, liquid, food product, food bar, container of liquid of defined volume, or other forms described herein, packaged for one-time consumption or administration.

Methods of Treatment

According to the methods of the disclosure, the compositions may be administered to a subject to treat (i) ADD/ADHD and related disorders, including amelioration of ADD/ADHD and related symptoms; (ii) anxiety and related disorders, including amelioration of anxiety and related symptoms; and (iii) depression and related disorders, including amelioration of depression and related symptoms. Advantageously, the compositions disclosed herein provide an over the counter and side effect-free treatment option for children, adolescents and adults afflicted with ADD, ADHD, and related disorders; and anxiety and depression.

In some embodiments, the present disclosure relates to a method for the treatment and/or prevention of ADHD, comprising the administration of a therapeutically effective amount of a natural product component, alone or in combination with a pharmaceutically acceptable carrier or excipient. In some embodiments, the method comprises administering a natural product composition comprising (i) passion flower in an amount ranging from between about 5% to about 17.5% by total weight of the natural product composition; (ii) a root extract from a *valerian* species in an amount ranging from between about 30% to about 60% by total weight of the natural product composition; (iii) Ashwagandha in an amount ranging from between about 10% to about 30% by total weight of the natural product composition; (iv) spikenard in an amount ranging from between about 5% to about 20% by total weight of the natural product composition; and (v) cannabidiol in an amount ranging from between about 2% to about 20% by total weight of the natural product composition. In some embodiments, the method comprises administering a natural product composition, such as denoted herein, together with a pharmaceutically acceptable excipient, carrier, and/or additive. In some embodiments, the method comprises administered a natural product composition embedded within a food composition or food product. In some embodiments, the method comprises co-administering another agent for treating ADD or ADHD or for mitigating symptoms of ADD or ADHD.

In some embodiments, the present disclosure relates to a method for the treatment and/or prevention of ADHD of predominantly impulsivity type, comprising the administration of a therapeutically effective amount of a natural product component, alone or in combination with a pharmaceutically acceptable carrier or excipient. In some embodiments, the method comprising administering a natural product composition comprising (i) passion flower in an amount ranging from between about 5% to about 17.5% by total weight of the natural product composition; (ii) a root extract from a *valerian* species in an amount ranging from between about 30% to about 60% by total weight of the natural product composition; (iii) Ashwagandha in an amount ranging from between about 10% to about 30% by total weight of the natural product composition; (iv) spikenard in an amount ranging from between about 5% to about 20% by total weight of the natural product composition; and (v) cannabidiol in an amount ranging from between about 2% to about 20% by total weight of the natural product composition. In some embodiments, the method comprises administering a natural product composition, such as denoted herein, together with a pharmaceutically acceptable excipient, carrier, and/or additive. In some embodiments, the method comprises administered a natural product composition embedded within a food composition or food product.

In some embodiments, the present disclosure relates to a method for the treatment and/or prevention of ADHD of predominantly inattentive type, comprising the administration of a therapeutically effective amount of a natural product component, alone or in combination with a pharmaceutically acceptable carrier or excipient. In some embodiments, the method comprising administering a natural product composition comprising (i) passion flower in an amount ranging from between about 5% to about 17.5% by total weight of the natural product composition; (ii) a root extract from a *valerian* species in an amount ranging from between about 30% to about 60% by total weight of the natural product composition; (iii) Ashwagandha in an amount ranging from between about 10% to about 30% by total weight of the natural product composition; (iv) spikenard in an amount ranging from between about 5% to about 20% by total weight of the natural product composition; and (v) cannabidiol in an amount ranging from between about 2% to about 20% by total weight of the natural product composition. In some embodiments, the method comprises administering a natural product composition, such as denoted herein, together with a pharmaceutically acceptable excipient, carrier, and/or additive. In some embodiments, the method comprises administered a natural product composition embedded within a food composition or food product.

In some embodiments, the present disclosure relates to a method for the treatment and/or prevention of ADHD of predominantly hyperactive-impulsive type, comprising the administration of a therapeutically effective amount of a natural product component, alone or in combination with a pharmaceutically acceptable carrier or excipient. In some embodiments, the method comprising administering a natural product composition comprising (i) passion flower in an amount ranging from between about 5% to about 17.5% by total weight of the natural product composition; (ii) a root extract from a *valerian* species in an amount ranging from between about 30% to about 60% by total weight of the natural product composition; (iii) Ashwagandha in an amount ranging from between about 10% to about 30% by total weight of the natural product composition; (iv) spikenard in an amount ranging from between about 5% to about 20% by total weight of the natural product composition; and (v) cannabidiol in an amount ranging from between about 2% to about 20% by total weight of the natural product composition. In some embodiments, the method comprises administering a natural product composition, such as denoted herein, together with a pharmaceutically acceptable excipient, carrier, and/or additive. In some embodiments, the method comprises administered a natural product composition embedded within a food composition or food product.

In some embodiments, the present disclosure relates to a method for the treatment and/or prevention of anxiety, comprising the administration of a therapeutically effective amount of a natural product component, alone or in combination with a pharmaceutically acceptable carrier or excipient. In some embodiments, the method comprises administering a natural product composition comprising (i) passion flower in an amount ranging from between about 5% to about 17.5% by total weight of the natural product composition; (ii) a root extract from a *valerian* species in an amount ranging from between about 30% to about 60% by total weight of the natural product composition; (iii) Ashwagandha in an amount ranging from between about 10% to about 30% by total weight of the natural product composition; (iv) spikenard in an amount ranging from between about 5% to about 20% by total weight of the natural product composition; and (v) cannabidiol in an amount ranging from between about 2% to about 20% by total weight of the natural product composition. In some embodiments, the method comprises administering a natural product composition, such as denoted herein, together with a pharmaceutically acceptable excipient, carrier, and/or additive. In some embodiments, the method comprises administered a natural product composition embedded within a food composition or food product.

In some embodiments, the present disclosure relates to a method for the treatment and/or prevention of depression, comprising the administration of a therapeutically effective amount of a natural product component, alone or in combination with a pharmaceutically acceptable carrier or excipient. In some embodiments, the method comprises administering a natural product composition comprising (i) passion flower in an amount ranging from between about 5% to about 17.5% by total weight of the natural product composition; (ii) a root extract from a *valerian* species in an amount ranging from between about 30% to about 60% by total weight of the natural product composition; (iii) Ashwagandha in an amount ranging from between about 10% to about 30% by total weight of the natural product composition; (iv) spikenard in an amount ranging from between about 5% to about 20% by total weight of the natural product composition; and (v) cannabidiol in an amount ranging from between about 2% to about 20% by total weight of the natural product composition. In some embodiments, the method comprises administering a natural product composition, such as denoted herein, together with a pharmaceutically acceptable excipient, carrier, and/or additive. In some embodiments, the method comprises administered a natural product composition embedded within a food composition or food product.

In some embodiments, the natural product compositions disclosed herein may be administered in a combination therapy, i.e., either simultaneously in single or separate dosage forms or in separate dosage forms within hours or days of each other. Examples of compounds/drugs used in such combination therapies for the treatment of ADD or ADHD include without limitation, Dextroamphetamine Sulf-Saccharate, Dextroamphetamine Sulfate, Dexmethylphenidate HCL, Methylphenidate HCL, Methylphenidate, Amphetamine Sulfate, Lisdexamfetamine Dimesylate, Clonidine HCL, Clonidine, Guanfacine HCL, Atomoxetine HCL, Guanfacine HCL, Nortriptyline HCL, Desipramine HCL, Imipramine HCL, and Bupropion HCL.

In some embodiments, the natural product compositions disclosed herein may be administered in a combination therapy, i.e., either simultaneously in single or separate dosage forms or in separate dosage forms within hours or days of each other. Examples of compounds/drugs used in such combination therapies for the treatment of anxiety include without limitation, Citalopram, Duloxetine, Escitalopram, Fluoxetine, Fluvoxamine, Paroxetine, Sertraline, Trazodone, Venlafaxine, Clomipramine, Desipramine, Doxepin, Imipramine, Isocarboxazid, Phenelzine, Selegiline, Tranylcypromine, Alprazolam, Chlordiazepoxide, Clonazepam, Diazepam, Lorazepam, Oxazepam, Divalproex, Gabapentin, Pregabalin, Atenolol, Nadolol, Propranolol, Molindone, Olanzapine, Quetiapine, and Risperidone. In some embodiments, the natural product compositions disclosed herein may be administered in a combination therapy, i.e., either simultaneously in single or separate dosage forms or in separate dosage forms within hours or days of each other. Examples of compounds/drugs used in such combination therapies for the treatment of depression include without limitation, selective serotonin reuptake inhibitors (SSRIs), serotonin and norepinephrine reuptake inhibitors (SNRIs), tricyclic antidepressants (TCAs), tetracyclic antidepressants, dopamine reuptake blockers, 5-HT1A receptor antagonists, 5-HT2 receptor antagonists, 5-HT3 receptor antagonists, monoamine oxidase inhibitors (MAOIs), and noradrenergic antagonists. Specific examples of anti-depressants include, but are not limited to, desvenlafaxine, duloxetine, levomilnacipran, venlafaxine, amitriptyline, amoxapine, clomipramine, desipramine, doxepin, imipramine, nortriptyline, protriptyline, trimipramine, bupropion, maprotiline, vilazodone, nefazodone, trazodone, vortioxetine, isocarboxazid, phenelzine, selegiline, tranylcypromine, and mirtazapine.

Stability

In some embodiments, the individual components of the natural product compositions of the present disclosure do not degrade to an unacceptable extent such that the final product has a shelf-life of at least about 2 years. As previously mentioned, this means that the active components within the dosage form remains within 90-110% of its initial amount in the dosage form during the desired (e.g., labeled) shelf-life of the dosage form (e.g., a minimum of 2 years after the date of manufacture of the dosage form). In some embodiments, the natural product compositions described herein can have a shelf half-life of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, 200, 210, 240, 270, 300, 330, or 360 days. In some cases, the natural product compositions described herein can have a shelf half-life of at least about 1, 2, 3, 4, or 5 years.

Additional Embodiments

A natural product composition comprising (i) passion flower in an amount ranging from between about 5% to about 17.5% by total weight of the natural product composition; (ii) a root extract from a *valerian* species in an amount ranging from between about 30% to about 60% by total weight of the natural product composition; (iii) Ashwagandha in an amount ranging from between about 10% to about 30% by total weight of the natural product composition; (iv) spikenard in an amount ranging from between about 5% to about 20% by total weight of the natural product composition; and (v) cannabidiol in an amount ranging from between about 2% to about 20% by total weight of the natural product composition.

A formulation comprising a natural product composition comprising (i) passion flower in an amount ranging from between about 5% to about 17.5% by total weight of the natural product composition; (ii) a root extract from a *valerian* species in an amount ranging from between about 30% to about 60% by total weight of the natural product composition; (iii) Ashwagandha in an amount ranging from between about 10% to about 30% by total weight of the natural product composition; (iv) spikenard in an amount ranging from between about 5% to about 20% by total weight of the natural product composition; and (v) cannabidiol in an amount ranging from between about 2% to about 20% by total weight of the natural product composition; and a pharmaceutically acceptable excipient or carrier.

A method of treating ADHD comprising administering a therapeutically effective dose of a formulation to a patient in need to treatment thereof, the formulation comprising a natural product composition comprising (i) passion flower in an amount ranging from between about 5% to about 17.5% by total weight of the natural product composition; (ii) a root extract from a *valerian* species in an amount ranging from between about 30% to about 60% by total weight of the natural product composition; (iii) Ashwagandha in an amount ranging from between about 10% to about 30% by total weight of the natural product composition; (iv) spikenard in an amount ranging from between about 5% to about 20% by total weight of the natural product composition; and (v) cannabidiol in an amount ranging from between about 2% to about 20% by total weight of the natural product composition; and a pharmaceutically acceptable excipient or carrier.

A method of mitigating the symptoms of ADHD comprising administering a therapeutically effective dose of a formulation to a patient in need thereof, the formulation comprising a natural product composition comprising (i) passion flower in an amount ranging from between about 5% to about 17.5% by total weight of the natural product composition; (ii) a root extract from a *valerian* species in an amount ranging from between about 30% to about 60% by total weight of the natural product composition; (iii) Ashwagandha in an amount ranging from between about 10% to about 30% by total weight of the natural product composition; (iv) spikenard in an amount ranging from between about 5% to about 20% by total weight of the natural product composition; and (v) cannabidiol in an amount ranging from between about 2% to about 20% by total weight of the natural product composition; and a pharmaceutically acceptable excipient or carrier.

A method of delaying the onset of symptoms associated with ADHD comprising administering a therapeutically effective dose of a formulation to a patient in need thereof, the formulation comprising a natural product composition comprising (i) passion flower in an amount ranging from between about 5% to about 17.5% by total weight of the natural product composition; (ii) a root extract from a *valerian* species in an amount ranging from between about 30% to about 60% by total weight of the natural product composition; (iii) Ashwagandha in an amount ranging from between about 10% to about 30% by total weight of the natural product composition; (iv) spikenard in an amount ranging from between about 5% to about 20% by total weight of the natural product composition; and (v) cannabidiol in an amount ranging from between about 2% to about 20% by total weight of the natural product composition; and a pharmaceutically acceptable excipient or carrier.

A composition comprising: (a) a natural product composition comprising (i) passion flower in an amount ranging from between about 5% to about 17.5% by total weight of the natural product composition; (ii) a root extract from a *valerian* species in an amount ranging from between about 30% to about 60% by total weight of the natural product composition; (iii) Ashwagandha in an amount ranging from between about 10% to about 30% by total weight of the natural product composition; (iv) spikenard in an amount ranging from between about 5% to about 20% by total weight of the natural product composition; and (v) cannabidiol in an amount ranging from between about 2% to about 20% by total weight of the natural product composition; (b) and another active pharmaceutical ingredient, for the treatment of ADHD.

A food product comprising a natural product composition comprising (i) passion flower in an amount ranging from between about 5% to about 17.5% by total weight of the natural product composition; (ii) a root extract from a *valerian* species in an amount ranging from between about 30% to about 60% by total weight of the natural product composition; (iii) Ashwagandha in an amount ranging from between about 10% to about 30% by total weight of the natural product composition; (iv) spikenard in an amount ranging from between about 5% to about 20% by total weight of the natural product composition; and (v) cannabidiol in an amount ranging from between about 2% to about 20% by total weight of the natural product composition. In some embodiments, the natural product composition of claim 1 is admixed with a gelatin-based foodstuff.

A method of treating anxiety comprising administering a therapeutically effective dose of a formulation to a patient in need of treatment thereof, the formulation comprising a natural product composition comprising (i) passion flower in an amount ranging from between about 5% to about 17.5% by total weight of the natural product composition; (ii) a root extract from a *valerian* species in an amount ranging from between about 30% to about 60% by total weight of the natural product composition; (iii) Ashwagandha in an amount ranging from between about 10% to about 30% by total weight of the natural product composition; (iv) spikenard in an amount ranging from between about 5% to about 20% by total weight of the natural product composition; and (v) cannabidiol in an amount ranging from between about 2% to about 20% by total weight of the natural product composition; and a pharmaceutically acceptable excipient or carrier.

A method of mitigating the symptoms of anxiety comprising administering a therapeutically effective dose of a formulation to a patient in need thereof, the formulation comprising a natural product composition comprising (i) passion flower in an amount ranging from between about 5% to about 17.5% by total weight of the natural product composition; (ii) a root extract from a *valerian* species in an amount ranging from between about 30% to about 60% by total weight of the natural product composition; (iii) Ashwagandha in an amount ranging from between about 10% to about 30% by total weight of the natural product composition; (iv) spikenard in an amount ranging from between about 5% to about 20% by total weight of the natural product composition; and (v) cannabidiol in an amount ranging from between about 2% to about 20% by total weight of the natural product composition; and a pharmaceutically acceptable excipient or carrier.

A method of delaying the onset of symptoms associated with anxiety comprising administering a therapeutically effective dose of a to a patient in need thereof, the formulation comprising a natural product composition comprising (i) passion flower in an amount ranging from between about 5% to about 17.5% by total weight of the natural product composition; (ii) a root extract from a *valerian* species in an amount ranging from between about 30% to about 60% by total weight of the natural product composition; (iii) Ashwagandha in an amount ranging from between about 10% to about 30% by total weight of the natural product composition; (iv) spikenard in an amount ranging from between about 5% to about 20% by total weight of the natural product composition; and (v) cannabidiol in an amount ranging from between about 2% to about 20% by total weight of the natural product composition; and a pharmaceutically acceptable excipient or carrier.

A method of treating depression comprising administering a therapeutically effective dose of a formulation a patient in need thereof, the formulation comprising a natural product composition comprising (i) passion flower in an amount ranging from between about 5% to about 17.5% by total weight of the natural product composition; (ii) a root extract from a *valerian* species in an amount ranging from between about 30% to about 60% by total weight of the natural product composition; (iii) Ashwagandha in an amount ranging from between about 10% to about 30% by total weight of the natural product composition; (iv) spikenard in an amount ranging from between about 5% to about 20% by total weight of the natural product composition; and (v) cannabidiol in an amount ranging from between about 2% to about 20% by total weight of the natural product composition; and a pharmaceutically acceptable excipient or carrier.

A method of mitigating the symptoms of depression comprising administering a therapeutically effective dose of a formulation to a patient in need thereof, the formulation comprising a natural product composition comprising (i) passion flower in an amount ranging from between about 5% to about 17.5% by total weight of the natural product composition; (ii) a root extract from a *valerian* species in an amount ranging from between about 30% to about 60% by total weight of the natural product composition; (iii) Ashwagandha in an amount ranging from between about 10% to about 30% by total weight of the natural product composition; (iv) spikenard in an amount ranging from between about 5% to about 20% by total weight of the natural product composition; and (v) cannabidiol in an amount ranging from between about 2% to about 20% by total weight of the natural product composition; and a pharmaceutically acceptable excipient or carrier.

A method of delaying the onset of symptoms associated with depression comprising administering a therapeutically effective dose of a formulation to a patient in need thereof, the formulation comprising a natural product composition comprising (i) passion flower in an amount ranging from between about 5% to about 17.5% by total weight of the natural product composition; (ii) a root extract from a *valerian* species in an amount ranging from between about 30% to about 60% by total weight of the natural product composition; (iii) Ashwagandha in an amount ranging from between about 10% to about 30% by total weight of the natural product composition; (iv) spikenard in an amount ranging from between about 5% to about 20% by total weight of the natural product composition; and (v) cannabidiol in an amount ranging from between about 2% to about 20% by total weight of the natural product composition; and a pharmaceutically acceptable excipient or carrier.

A composition comprising a natural product mixture and another active pharmaceutical ingredient for the treatment of anxiety, the natural product mixture comprising (i) passion flower in an amount ranging from between about 5% to about 17.5% by total weight of the natural product composition; (ii) a root extract from a *valerian* species in an amount ranging from between about 30% to about 60% by total weight of the natural product composition; (iii) Ashwagandha in an amount ranging from between about 10% to about 30% by total weight of the natural product composition; (iv) spikenard in an amount ranging from between about 5% to about 20% by total weight of the natural product composition; and (v) cannabidiol in an amount ranging from between about 2% to about 20% by total weight of the natural product composition.

A composition comprising the natural product mixture and another active pharmaceutical ingredient for the treatment of depression, the natural product mixture comprising (i) passion flower in an amount ranging from between about 5% to about 17.5% by total weight of the natural product composition; (ii) a root extract from a *valerian* species in an amount ranging from between about 30% to about 60% by total weight of the natural product composition; (iii) Ashwagandha in an amount ranging from between about 10% to about 30% by total weight of the natural product composition; (iv) spikenard in an amount ranging from between about 5% to about 20% by total weight of the natural product composition; and (v) cannabidiol in an amount ranging from between about 2% to about 20% by total weight of the natural product composition.

A natural product composition comprising cannabidiol and a hemp oil. In some embodiments, the natural product comprising further compries at least one of passion flower, a root extract from a *valerian* species, Ashwagandha, and spikenard. In some embodiments, the natural product comprising further compries at least two of passion flower, a root extract from a *valerian* species, Ashwagandha, and spikenard. In some embodiments, the natural product comprising further compries at least three of passion flower, a root extract from a *valerian* species, Ashwagandha, and spikenard. In some embodiments, the natural product comprising further compries passion flower, a root extract from a *valerian* species, Ashwagandha, and spikenard.

A natural product consisting essentially of comprising cannabidiol and a hemp oil.

A formulation comprising a natural product composition and a pharmaceutically acceptable excipient or carrier, wherein the natural product comprises cannabidiol and a hemp oil. In some embodiments, the natural product comprising further compries at least one of passion flower, a root extract from a *valerian* species, Ashwagandha, and spikenard. In some embodiments, the natural product comprising further compries at least two of passion flower, a root extract from a *valerian* species, Ashwagandha, and spikenard. In some embodiments, the natural product comprising further compries at least three of passion flower, a root extract from a *valerian* species, Ashwagandha, and spikenard. In some embodiments, the natural product comprising further compries passion flower, a root extract from a *valerian* species, Ashwagandha, and spikenard.

A method of treating ADHD comprising administering a therapeutically effective dose of a formulation to a patient in need thereof, the formulation comprising cannabidiol and a hemp oil. In some embodiments, the natural product formulation further comprises at least one of passion flower, a root extract from a *valerian* species, Ashwagandha, and spikenard. In some embodiments, the natural product formulation further comprises at least two of passion flower, a root extract from a *valerian* species, Ashwagandha, and spikenard. In some embodiments, the natural product formulation further comprises at least three of passion flower, a root extract from a *valerian* species, Ashwagandha, and spikenard. In some embodiments, the natural product formulation further comprises passion flower, a root extract from a *valerian* species, Ashwagandha, and spikenard.

A method of mitigating the symptoms of ADHD comprising administering a therapeutically effective dose of a formulation to a patient in need thereof, the formulation comprising cannabidiol and a hemp oil. In some embodiments, the natural product formulation further comprises at least one of passion flower, a root extract from a *valerian* species, Ashwagandha, and spikenard. In some embodiments, the natural product formulation further comprises at least two of passion flower, a root extract from a *valerian* species, Ashwagandha, and spikenard. In some embodiments, the natural product formulation further comprises at least three of passion flower, a root extract from a *valerian* species, Ashwagandha, and spikenard. In some embodiments, the natural product formulation further comprises passion flower, a root extract from a *valerian* species, Ashwagandha, and spikenard.

A method of delaying the onset of symptoms associated with ADHD comprising administering a therapeutically effective dose of a formulation to a patient in need thereof, the formulation comprising cannabidiol and a hemp oil. In some embodiments, the natural product formulation further comprises at least one of passion flower, a root extract from a *valerian* species, Ashwagandha, and spikenard. In some embodiments, the natural product formulation further comprises at least two of passion flower, a root extract from a *valerian* species, Ashwagandha, and spikenard. In some embodiments, the natural product formulation further comprises at least three of passion flower, a root extract from a *valerian* species, Ashwagandha, and spikenard. In some embodiments, the natural product formulation further comprises passion flower, a root extract from a *valerian* species, Ashwagandha, and spikenard.

A composition comprising a natural product composition and at least one additional active pharmaceutical ingredient for the treatment of ADHD, the natural product composition comprising a cannabidiol and a hemp oil. In some embodiments, the natural product composition further comprises at least one of passion flower, a root extract from a *valerian* species, Ashwagandha, and spikenard. In some embodiments, the natural product composition further comprises at least two of passion flower, a root extract from a *valerian* species, Ashwagandha, and spikenard. In some embodiments, the natural product composition further comprises at least three of passion flower, a root extract from a *valerian* species, Ashwagandha, and spikenard. In some embodiments, the natural product composition further comprises passion flower, a root extract from a *valerian* species, Ashwagandha, and spikenard.

A food product comprising a natural product composition comprising a cannabidiol and a hemp oil. In some embodiments, the natural product composition further comprises at least one of passion flower, a root extract from a *valerian* species, Ashwagandha, and spikenard. In some embodiments, the natural product composition further comprises at least two of passion flower, a root extract from a *valerian* species, Ashwagandha, and spikenard. In some embodiments, the natural product composition further comprises at least three of passion flower, a root extract from a *valerian* species, Ashwagandha, and spikenard. In some embodiments, the natural product composition further comprises passion flower, a root extract from a *valerian* species, Ashwagandha, and spikenard. In some embodiments, the natural product composition of is admixed with a gelatin-based foodstuff.

A method of treating anxiety comprising administering a therapeutically effective dose of a formulation to a patient in need thereof, the formulation comprising cannabidiol and a hemp oil. In some embodiments, the natural product formulation further comprises at least one of passion flower, a root extract from a *valerian* species, Ashwagandha, and spikenard. In some embodiments, the natural product formulation further comprises at least two of passion flower, a root extract from a *valerian* species, Ashwagandha, and spikenard. In some embodiments, the natural product formulation further comprises at least three of passion flower, a root extract from a *valerian* species, Ashwagandha, and spikenard. In some embodiments, the natural product formulation further comprises passion flower, a root extract from a *valerian* species, Ashwagandha, and spikenard.

A method of mitigating the symptoms of anxiety comprising administering a therapeutically effective dose of a formulation to a patient in need thereof, the formulation comprising cannabidiol and a hemp oil. In some embodiments, the natural product formulation further comprises at least one of passion flower, a root extract from a *valerian* species, Ashwagandha, and spikenard. In some embodiments, the natural product formulation further comprises at least two of passion flower, a root extract from a *valerian* species, Ashwagandha, and spikenard. In some embodiments, the natural product formulation further comprises at least three of passion flower, a root extract from a *valerian* species, Ashwagandha, and spikenard. In some embodiments, the natural product formulation further comprises passion flower, a root extract from a *valerian* species, Ashwagandha, and spikenard.

A method of delaying the onset of symptoms associated with anxiety comprising administering a therapeutically effective dose of a formulation to a patient in need thereof, the formulation comprising cannabidiol and a hemp oil. In some embodiments, the natural product formulation further comprises at least one of passion flower, a root extract from a *valerian* species, Ashwagandha, and spikenard. In some embodiments, the natural product formulation further comprises at least two of passion flower, a root extract from a *valerian* species, Ashwagandha, and spikenard. In some embodiments, the natural product formulation further comprises at least three of passion flower, a root extract from a *valerian* species, Ashwagandha, and spikenard. In some embodiments, the natural product formulation further comprises passion flower, a root extract from a *valerian* species, Ashwagandha, and spikenard.

A method of treating depression comprising administering a therapeutically effective dose of a formulation to a patient in need thereof, the formulation comprising cannabidiol and a hemp oil. In some embodiments, the natural product formulation further comprises at least one of passion flower, a root extract from a *valerian* species, Ashwagandha, and spikenard. In some embodiments, the natural product formulation further comprises at least two of passion flower, a root extract from a *valerian* species, Ashwagandha, and spikenard. In some embodiments, the natural product formulation further comprises at least three of passion flower, a root extract from a *valerian* species, Ashwagandha, and spikenard. In some embodiments, the natural product formulation further comprises passion flower, a root extract from a *valerian* species, Ashwagandha, and spikenard.

A method of mitigating the symptoms of depression comprising administering a therapeutically effective dose of a to a patient in need thereof, the formulation comprising cannabidiol and a hemp oil. In some embodiments, the natural product formulation further comprises at least one of passion flower, a root extract from a *valerian* species, Ashwagandha, and spikenard. In some embodiments, the natural product formulation further comprises at least two of passion flower, a root extract from a *valerian* species, Ashwagandha, and spikenard. In some embodiments, the natural product formulation further comprises at least three of passion flower, a root extract from a *valerian* species, Ashwagandha, and spikenard. In some embodiments, the natural product formulation further comprises passion flower, a root extract from a *valerian* species, Ashwagandha, and spikenard.

A method of delaying the onset of symptoms associated with depression comprising administering a therapeutically effective dose of a formulation to a patient in need thereof, the formulation comprising cannabidiol and a hemp oil. In some embodiments, the natural product formulation further comprises at least one of passion flower, a root extract from a *valerian* species, Ashwagandha, and spikenard. In some embodiments, the natural product formulation further comprises at least two of passion flower, a root extract from a *valerian* species, Ashwagandha, and spikenard. In some embodiments, the natural product formulation further comprises at least three of passion flower, a root extract from a *valerian* species, Ashwagandha, and spikenard. In some embodiments, the natural product formulation further comprises passion flower, a root extract from a *valerian* species, Ashwagandha, and spikenard.

A composition comprising a natural product composition and at least one other active pharmaceutical ingredient for the treatment of anxiety, the natural product composition comprising a cannabidiol and a hemp oil. In some embodiments, the natural product composition further comprises at least one of passion flower, a root extract from a *valerian* species, Ashwagandha, and spikenard. In some embodiments, the natural product composition further comprises at least two of passion flower, a root extract from a *valerian* species, Ashwagandha, and spikenard. In some embodiments, the natural product composition further comprises at least three of passion flower, a root extract from a *valerian* species, Ashwagandha, and spikenard. In some embodiments, the natural product composition further comprises passion flower, a root extract from a *valerian* species, Ashwagandha, and spikenard.

A composition comprising a natural product composition and at least one other active pharmaceutical ingredient for the treatment of depression, the natural product composition comprising a cannabidiol and a hemp oil. In some embodiments, the natural product composition further comprises at least one of passion flower, a root extract from a *valerian* species, Ashwagandha, and spikenard. In some embodiments, the natural product composition further comprises at least two of passion flower, a root extract from a *valerian* species, Ashwagandha, and spikenard. In some embodiments, the natural product composition further comprises at least three of passion flower, a root extract from a *valerian* species, Ashwagandha, and spikenard. In some embodiments, the natural product composition further comprises passion flower, a root extract from a *valerian* species, Ashwagandha, and spikenard.

Example 1—The following table provides an exemplary embodiment of a natural product composition of the present disclosure.

| Active Component | Percent by total weight of the natural product composition |
|---|---|
| Cannabidiol | 9% |
| Spikenard | 13% |
| root extract from a Valerian species | 44% |
| passion flower extract | 11% |
| Ashwagandha | 22% |

Example 2—The following table provides an exemplary embodiment of a single dose of a natural product composition.

| Active Component | Amount in a suitable dosage unit (mg) |
|---|---|
| Cannabidiol | 200 mg |
| Spikenard | 300 mg |
| root extract from a Valerian species | 1000 mg |
| passion flower extract | 250 mg |
| Ashwagandha | 500 mg |

Example 3—The table below sets forth exemplary dosage amounts for a pediatric patient.

| Active Component | Dosage |
|---|---|
| Cannabidiol | 6 mg/kg/day |
| Spikenard | 9 mg/kg/day |
| root extract from a Valerian species | 20 mg/kg/day |
| passion flower extract | 7.5 mg/kg/day |
| Ashwagandha | 15 mg/kg/day |

Example 4—The table below sets forth exemplary dosage amounts for an adult patient.

| Active Component | Dosage |
|---|---|
| Cannabidiol | 8 mg/kg/day |
| Spikenard | 12 mg/kg/day |
| root extract from a Valerian species | 30 mg/kg/day |
| passion flower extract | 10 mg/kg/day |
| Ashwagandha | 20 mg/kg/day |

The invention claimed is:

1. A natural product composition comprising (i) a therapeutically effective amount of a cannabidiol or a metabolite of the cannabidiol or a precursor of the cannabidiol; (ii) a medium chain triglyceride; and (iii) and a therapeutically effective amount of at least one additional active component, wherein the at least one additional active component is selected from the group consisting of passion flower, a root extract from a *valerian* species, ashwagandha, and spikenard.

2. The natural product composition of claim 1, wherein the at least one additional active component comprises at least two of passion flower, a root extract from a *valerian* species, Ashwagandha, and spikenard.

3. The natural product composition of claim 1, wherein the at least one additional active component comprises at least three of passion flower, a root extract from a *valerian* species, Ashwagandha, and spikenard.

4. The natural product of claim 1, wherein the cannabidiol comprises 2-[3-methyl-6-(1-methylethenyl)-2-cyclohexen-1-yl]-5-pentyl-1,3-benzenediol or a salt, or a solvate thereof.

5. The natural product of claim 1, wherein the cannabidiol metabolite comprises a metaboloite of 2-[3-methyl-6-(1-methylethenyl)-2-cyclohexen-1-yl]-5-pentyl-1,3-benzenediol or a salt, or a solvate thereof.

6. The natural product of claim 1, wherein the cannabidiol comprises a metabolic precursor of 2-[3-methyl-6-(1-methylethenyl)-2-cyclohexen-1-yl]-5-pentyl-1,3-benzenediol or a salt, or a solvate thereof.

7. The natural product claim 1, wherein the cannabidiol precursor is present in the natural product composition in an amount ranging from between about 2% to about 20% by total weight of the natural product composition.

8. The natural product claim 1, wherein the cannabidiol is present in the natural product composition in an amount ranging from between about 4% to about 15% by total weight of the natural product composition.

9. The natural product claim 1, wherein the cannabidiol is present in the natural product composition in an amount ranging from between about 6% to about 11% by total weight of the natural product composition.

10. The natural product composition of claim 1, wherein the natural product composition comprises hemp oil and wherein the cannabidiol is at least partially present in the hemp oil.

11. A natural product composition comprising (i) a cannabidiol, and (ii) and at least two additives selected from the group consisting of a compound derived or extracted from passion flower, a compound derived or extracted from *valerian* or *valerian* root, a compound derived or extracted from ashwagandha, and a compound derived or extracted from spikenard.

12. The natural product composition of claim 11, wherein the natural product composition comprises hemp oil and wherein the cannabidiol is at least partially present in the hemp oil.

13. A natural product composition comprising (i) hemp oil, and (ii) and at least two additives selected from the group consisting of passion flower, a root extract from a *valerian* species, Ashwagandha, and spikenard.

\* \* \* \* \*